United States Patent
Martin

(10) Patent No.: US 9,789,003 B2
(45) Date of Patent: Oct. 17, 2017

(54) DEVICE FOR LASER TREATMENT OF A HUMAN EYE

(71) Applicant: Wavelight GmbH, Erlangen (DE)

(72) Inventor: Peter Martin, Erlangen (DE)

(73) Assignee: Wavelight GmbH (DE)

( * ) Notice: Subject to any disclaimer, the term of this patent is extended or adjusted under 35 U.S.C. 154(b) by 0 days.

(21) Appl. No.: 14/968,245

(22) Filed: Dec. 14, 2015

(65) Prior Publication Data

US 2016/0213517 A1  Jul. 28, 2016

(30) Foreign Application Priority Data

Jan. 26, 2015 (DE) .................. 10 2015 000 913

(51) Int. Cl.
*A61F 9/008* (2006.01)

(52) U.S. Cl.
CPC ...... *A61F 9/00804* (2013.01); *A61F 9/00836* (2013.01); *A61F 2009/00872* (2013.01); *A61F 2009/00897* (2013.01)

(58) Field of Classification Search
CPC .. A61F 2009/00872; A61F 2009/00897; A61F 9/00804; A61F 9/00836
USPC ............................................. 600/2, 4–5, 10
See application file for complete search history.

(56) References Cited

U.S. PATENT DOCUMENTS

| 6,344,040 | B1 | 2/2002 | Juhaz | |
|---|---|---|---|---|
| 2003/0212387 | A1* | 11/2003 | Kurtz | A61F 9/008 606/4 |
| 2004/0243111 | A1 | 12/2004 | Bendett et al. | |
| 2008/0319428 | A1 | 12/2008 | Wiechmann et al. | |
| 2011/0184394 | A1* | 7/2011 | Donitzky | A61F 9/008 606/5 |
| 2016/0008173 | A1* | 1/2016 | Krause | A61F 9/00836 606/5 |

FOREIGN PATENT DOCUMENTS

| CA | 2126667 | 11/2000 |
|---|---|---|
| CA | 2787768 | 7/2011 |
| CA | 2288134 | 11/2011 |
| EP | 1034757 A2 | 9/2000 |
| WO | 2009/152838 A1 | 12/2009 |
| WO | 2011/088848 A1 | 7/2011 |
| WO | 2013/004255 A1 | 1/2013 |
| WO | 2014/135218 A1 | 9/2014 |

* cited by examiner

*Primary Examiner* — Christopher A Flory
*Assistant Examiner* — Jonathan Kuo
(74) *Attorney, Agent, or Firm* — Keiko Ichiye

(57) ABSTRACT

An apparatus for treatment of an eye comprises a source of pulsed laser radiation, and a control device for controlling a focus of the laser radiation to generate an incision figure. The incision figure defines a corneal flap, a first auxiliary channel and a second auxiliary channel. The corneal flap is connected to adjoining corneal tissue in a hinge region, and has a flap underside parted-off from adjoining corneal tissue by a bed incision. The first auxiliary channel extends from the hinge region to an outer surface of the eye and is adapted to remove gases that develop during the generation of the bed incision. The second auxiliary channel extends along an edge of the bed incision, is connected to the first auxiliary channel, and extends beyond the hinge region. The control device is configured to generate the second auxiliary channel prior to the bed incision.

20 Claims, 3 Drawing Sheets

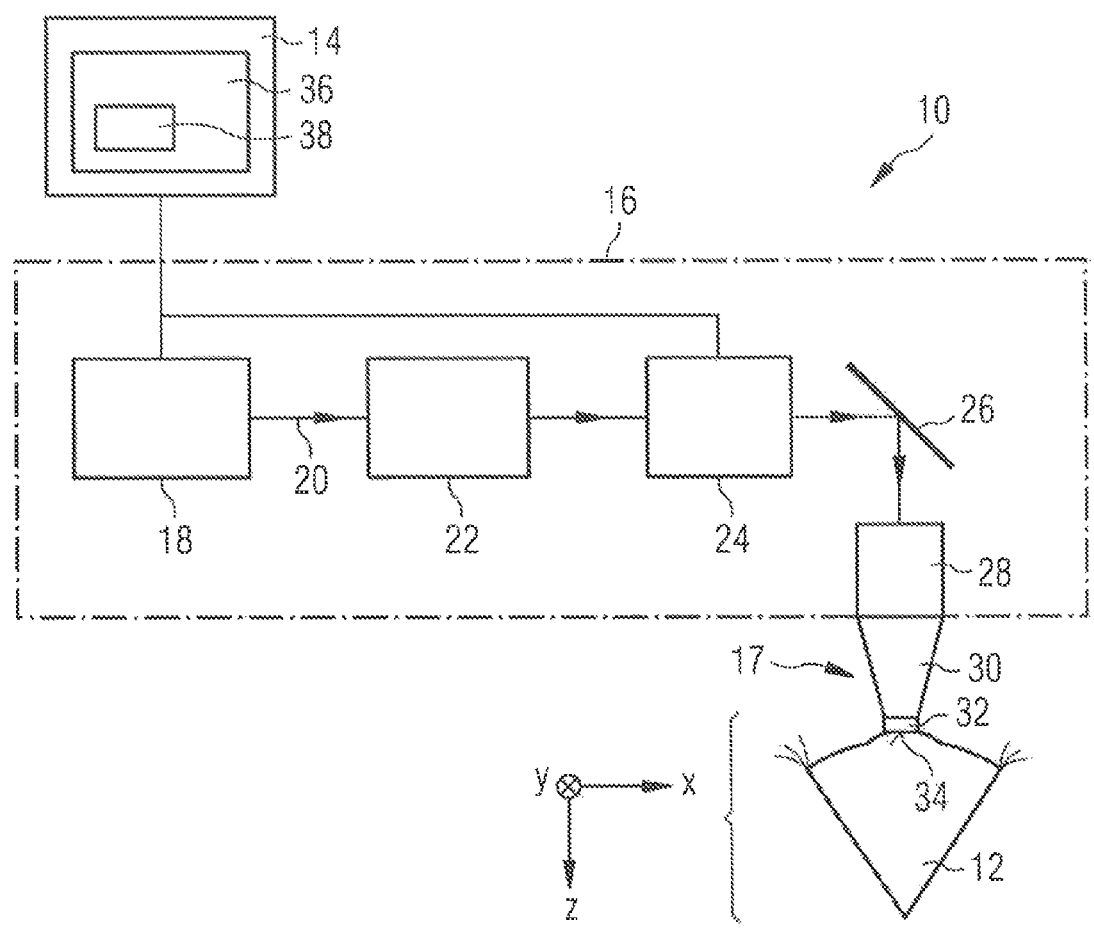

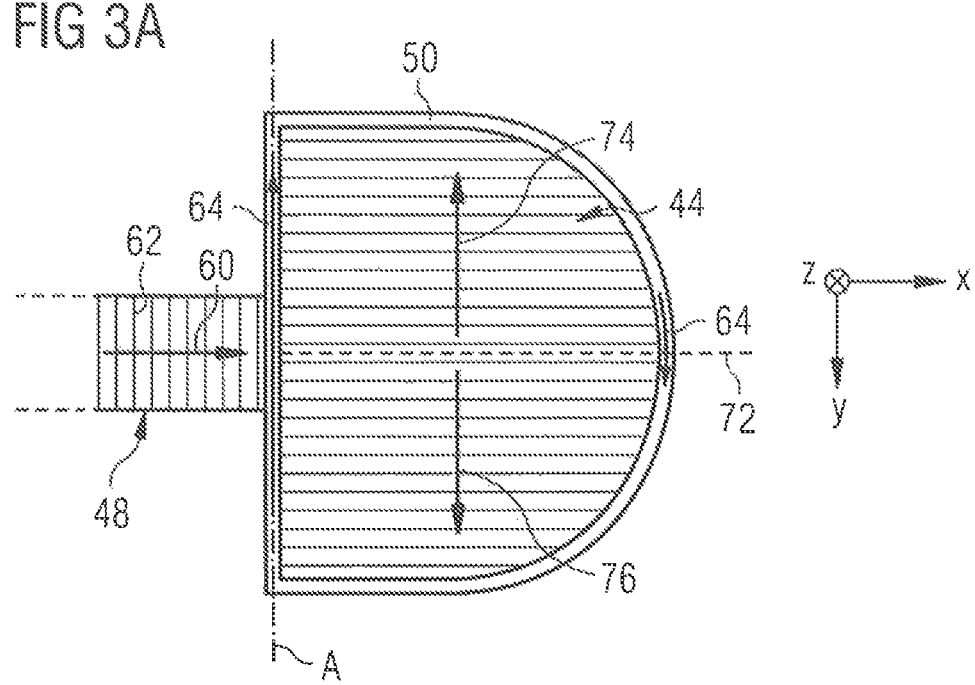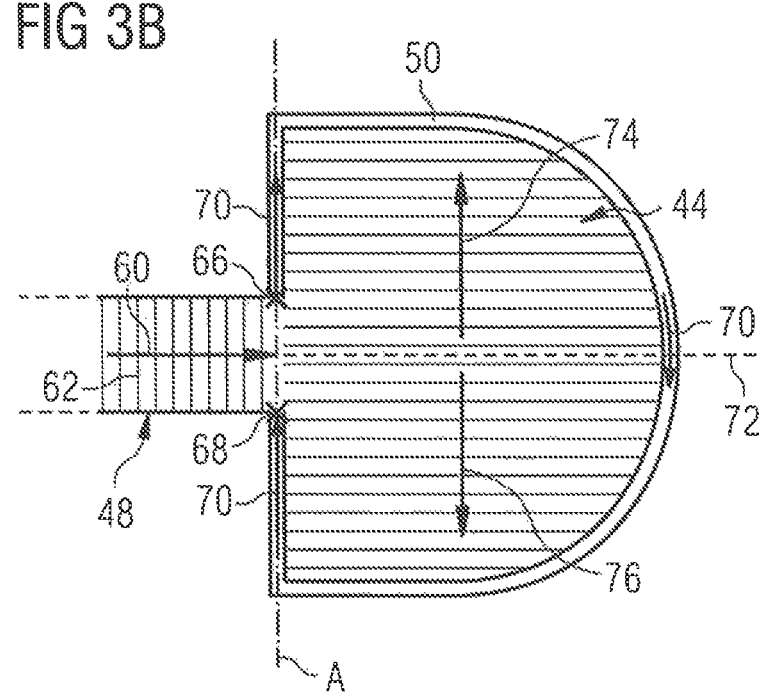

DEVICE FOR LASER TREATMENT OF A HUMAN EYE

CROSS REFERENCE TO RELATED APPLICATIONS

This application claims priority to German Patent Application Serial Number 10 2015 000 913.3, filed 26 Jan. 2015, titled "DEVICE FOR LASER TREATMENT OF A HUMAN EYE," which is hereby incorporated by reference in its entirety.

TECHNICAL FIELD

The present disclosure relates in general to the generation of incisions in a human cornea by means of focused, pulsed laser radiation. It relates in particular to the preparation of a LASIK flap whilst avoiding the generation of a so-called opaque bubble layer (OBL).

BACKGROUND

Frequently, a so-called LASIK (laser in-situ keratomileusis) technique is used to correct defects of vision of the human eye (for example, short-sightedness or long-sightedness or astigmatism). In this case, a small cover disk (generally referred to as a flap) is first parted off from adjoining corneal tissue, the flap remaining connected to the corneal tissue in a hinge region. This enables the flap to be easily folded away in order to expose the tissue regions of the cornea underneath, and enables the flap to be easily folded back following an ablation of the exposed tissue regions by means of focused UV laser radiation. Removal of material in the ablation procedure causes the surface of the cornea to have an altered shape, after the flap has been folded back, and thus causes the cornea, and consequently the eye system overall, to have a different refractive behaviour. Through appropriate definition of the ablation profile, it is possible to achieve an at least significant reduction in visual defectiveness and, at best, even almost complete correction.

To generate incisions by means of focussed laser radiation in transparent or translucent material (transparent/translucent for the laser radiation), the physical effect of so-called laser-induced optical breakdown is used. The breakdown results in a photodisruption of the irradiated tissue in the region of the focus of the laser radiation. The interaction of the incident laser radiation with the irradiated corneal tissue causes local vaporization of the tissue in the focal point. This may result in the development of gases, which—unless dissipated outwards—collect in internal cavities or are absorbed by adjoining corneal tissue. It has been found that, if gases that develop during production of the flap remain in the cornea in the case of LASIK treatment of the human eye, this may result in problems in the subsequent ablation procedure. In this case, the gases may result in development of a so-called opaque bubble layer (OBL). The development of an OBL may make it more difficult, or even impossible, to precisely track the eye by means of an eye tracker. It is to be noted in this case that laser systems used for the ablation of corneal tissue (as in a LASIK treatment) generally comprise an eye tracker, in order to capture eye movements during the laser treatment and to guide the laser radiation according to the captured movements. Normally, the eye trackers include at least one camera, and appropriate image analysis software for analysing the images recorded by the camera and for capturing changes in the eye position. In this case, characteristic features of the eye (for example, particular points on the iris and/or the center of the pupil and/or the apex of the cornea and/or the limbus) are analysed by the image analysis software. It has been found that gas accumulations (e.g. an OBL) remaining in the cornea, which have occurred during production of the flap, may impede the capturing of such characteristic features of the eye.

SUMMARY OF EXAMPLE EMBODIMENTS

An object of the present invention is to avoid, or at least reduce, the occurrence of an OBL in the case of production of the LASIK flap by laser means.

One aspect of the present invention is an apparatus for laser treatment of a human eye, comprising: a source of pulsed laser radiation; a control device configured to control a focus of the laser radiation in space and time to generate an incision figure that defines: a corneal flap connected to adjoining corneal tissue in a hinge region and having a flap underside parted-off from adjoining corneal tissue by a bed incision; a first auxiliary channel extending from the hinge region to an outer surface of the eye and adapted to remove gases that develop during the generation of the bed incision; and a second auxiliary channel extending along an edge of the bed incision, wherein the second auxiliary channel is connected to the first auxiliary channel and extends beyond the hinge region, wherein the control device is configured to generate the second auxiliary channel prior to the bed incision.

Even before production of the bed incision commences, the first auxiliary channel and the second auxiliary channel provide a possibility for removing gases that develop during the production of the bed incision. Thus, during each phase of the production of the bed incision, the gases can be removed out of the region of the bed incision in a simplified manner, via the second auxiliary channel, into the first auxiliary channel and towards the surface of the cornea.

It may be provided that the second auxiliary channel extends continuously into a region of the bed incision edge that is opposite the hinge region.

In this case, the second auxiliary channel may extend continuously over the entire part of the bed incision edge that is located outside of the hinge region. This improves the previously described removal of the gases to the effect that, in each region within the bed incision, the shortest possible distance to the second auxiliary channel is provided.

For an optimum removal of gases, it may further be provided that the second auxiliary channel forms a closed annular channel, which has a channel portion that runs rectilinearly in the hinge region, and runs in the form of an arc outside of the hinge region. In this case, the production of the rectilinear channel portion may be prescribed, at least partially, by the program instructions, before the production of the arcuate channel portion.

The second auxiliary channel may have a height that is substantially constant over its length. In this case, the height may describe a difference between a deeper corneal region and a less deep corneal region, starting from the surface of the cornea. Alternatively, the second auxiliary channel may have a height that varies over its length.

For simplified removal of gases through the second auxiliary channel, the height of the second auxiliary channel may correspond to a plurality of damage zones, produced by photodisruption, that are disposed above one another. As an alternative to this, it may be provided that the channel height of the second auxiliary channel corresponds only to a single damage zone produced by photodisruption. The second auxiliary channel may have, for example, a channel height of not less than 5 µm or 10 µm or 15 µm. Further, the second auxiliary channel may have, for example, a channel height of not more than 35 µm or 30 µm or 25 µm.

It may further be provided that the second auxiliary channel reaches into deeper corneal regions and less deep corneal regions, relative to the bed incision. As an alternative to this, the second auxiliary region may reach only into deeper corneal regions or less deep corneal regions, relative to the bed incision.

The flap defined by the incision figure may have a flap edge that is parted off from adjoining corneal tissue by a lateral incision located outside of the hinge region, wherein the control device is configured to cause generation of the lateral incision after the bed incision. As an alternative to this, the control device may be configured to cause generation of the lateral incision after the second auxiliary channel and before the bed incision. The lateral incision may adjoin the second auxiliary channel and lead as far as the eye surface. In this case, it may be provided that the lateral incision adjoins the second auxiliary channel rectilinearly.

To further improve the removal of the gases that develop during the generation of the bed incision, the control device may be configured to generate the bed incision through movement of the focus along a plurality of mutually parallel, rectilinear scan lines, wherein line directions of the scan lines extend transversely with respect to an imaginary hinge axis of the hinge region. In this case, the scan lines may run at least approximately perpendicularly in relation to the hinge axis. Thus, in particular, the gases in the region of the hinge axis can escape into the second auxiliary channel and into the first auxiliary channel in a simplified manner.

Further, the control device may be configured to cause, for a first group of scan lines, a progression of the focus from a scan line to a respectively next scan line of the first group in a first direction and, for a second group of scan lines, a progression of the focus from a scan line to a respectively next scan line of the second group in a direction opposite to the first direction. In this case, the first direction may correspond to a movement along the hinge axis.

It may be provided that an area of the bed incision is substantially divided by the first and second groups into halves adjoining one another at an imaginary center line perpendicular to the hinge axis, wherein for each of the first and second groups the progression of the focus is effected in a direction away from the center line.

The first auxiliary channel may extend into corneal depths beneath the bed incision. The portion of the first auxiliary incision that is located deeper in cornea, relative to the bed incision, may have a function of a gas reservoir. The gases that develop during the production of the bed incision can be stored temporarily by the gas reservoir when the removal capacity of the portion of the first auxiliary channel located less deeply in the cornea, relative to the bed incision, has been exhausted. It may further be provided that the first auxiliary channel extends into corneal depths beneath the second auxiliary channel, or that the point of the first auxiliary channel that is deepest in the cornea corresponds to the point of the second auxiliary channel that is deepest in the cornea.

Another aspect of the present invention is a method for laser treatment of a human eye, comprising steps of: providing pulsed laser radiation; directing the laser radiation at a human cornea to be treated; controlling a focus of the laser radiation in space and time to generate: a corneal flap connected to adjoining corneal tissue in a hinge region and having a flap underside parted-off from adjoining corneal tissue by a bed incision; a first auxiliary channel extending from the hinge region to an outer eye surface and adapted to remove gases that develop during the generation of the bed incision; and a second auxiliary channel extending along an edge of the bed incision, wherein the second auxiliary channel is connected to the first auxiliary channel and extends beyond the hinge region, wherein the second auxiliary channel is generated prior to the bed incision.

BRIEF DESCRIPTION OF THE DRAWINGS

Additional features, advantages or elements of the present invention may be gathered from the following description of the accompanying drawings, in which:

FIG. 1 shows a schematic block representation of an embodiment of a device for laser treatment of a human eye;

FIGS. 3A and 3B show embodiments of scan patterns of the focus movement according to the provided time sequence for producing a corneal incision figure.

DETAILED DESCRIPTION OF EXAMPLE EMBODIMENTS

Figure 2A:
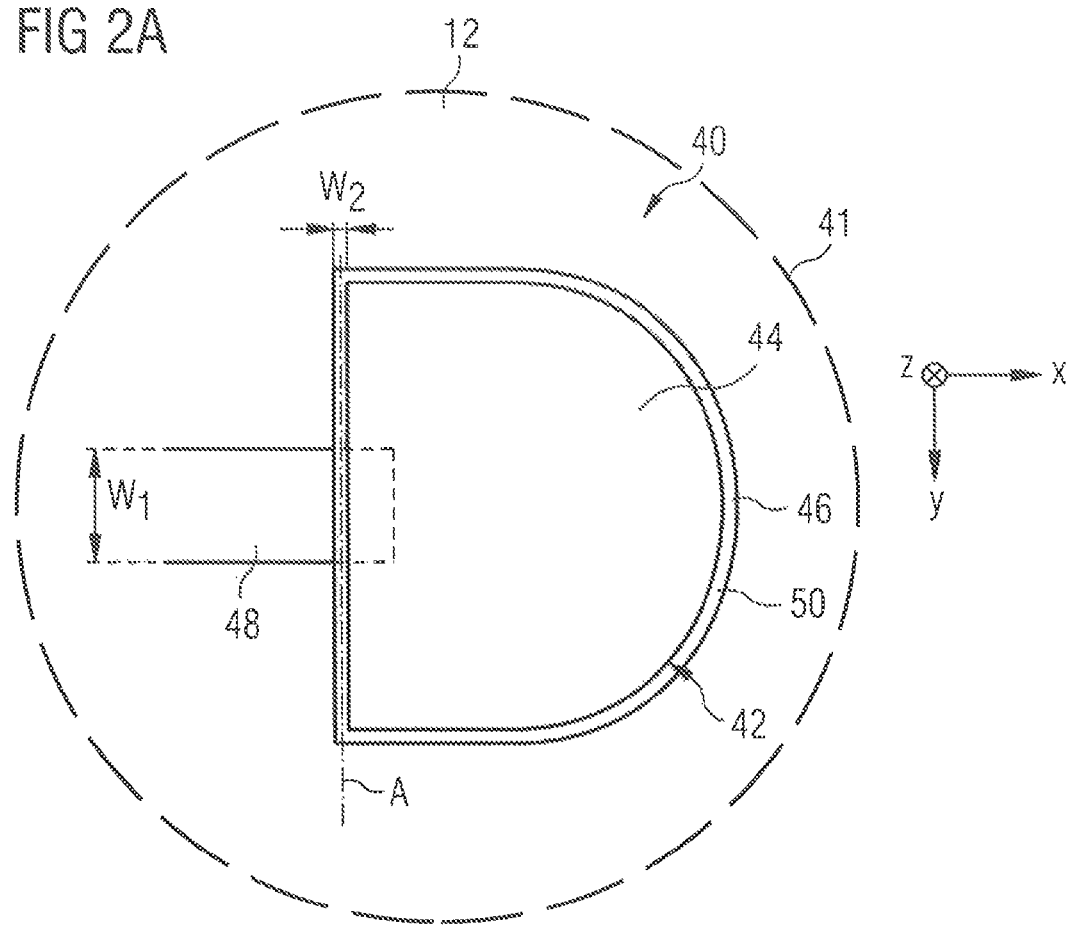
FIGS. 2A and 2B show embodiments of a corneal incision figure in the laser treatment of a human eye.

FIG. 1 shows a block representation of an embodiment of a device, denoted in general by 10, for laser treatment of a human eye 12. The device 10 in this case comprises a control device 14, a laser arrangement 16 and a patient adapter 17.

The laser arrangement 16 comprises a laser source 18, which generates a laser beam 20 having pulse durations that are, for example, in the femtosecond range. The laser beam has a suitable wavelength for producing a laser-induced optical breakdown in the corneal tissue of the eye 12. The laser beam 20 may have a wavelength in the range of from 300 nm (nanometers) to 1900 nm, e.g. a wavelength in the range of from 300 nm to 650 nm, 650 nm to 1050 nm, 1050 nm to 1250 nm, or 1100 nm to 1900 nm. The laser beam 20 may additionally have a focal diameter of 5 µm or less.

A beam expansion optical system 22, a scanner device 24, a mirror 26 and a focusing objective 28 are disposed behind the laser source 18 in the direction of propagation of the laser beam 20 (indicated by the arrows in FIG. 1). The beam expansion optical system 22 serves to enlarge the diameter of the laser beam 20 generated by the laser source 18. In the embodiment shown, the beam expansion optical system 22 is a Galilean telescope, which comprises a concave lens (lens having a negative refractive power), and a convex lens (lens having a positive refractive power) that is disposed behind the concave lens in the direction of propagation of the laser beam 20. The lenses may be a plano-concave lens and a plano-convex lens, whose planar sides are disposed facing towards each other. In another embodiment, the expansion optical system may comprise, as an alternative to the Galilean telescope, for example a Keplerian telescope, which has two convex lenses.

The scanner device 24 is designed to control the position of a focus of the laser beam 20 (radiation focus) in the transversal direction and in the longitudinal direction. In this case, the transversal direction describes the direction that is transverse in relation to the direction of propagation of the laser beam 20 (denoted as the x-y plane), and the longitudinal direction describes the direction of propagation of the laser beam 20 (denoted as the z-direction). For the purpose of transversally deflecting the laser beam 20, the scanning device 24 may comprise, for example, a pair of galvanometrically actuated deflection mirrors that can be tilted about mutually perpendicular axes. As an alternative or in addition to this, the scanner device 24 may have an electro-optical crystal or other components suitable for transversally deflecting the laser beam 20. The scanner device 24 may additionally comprise a lens that is longitudinally adjustable or that has a variable refractive power, or a deformable mirror, in order to influence the divergence of the laser beam 20 and, consequently, the longitudinal alignment of the radiation focus. In the embodiment shown, the components for controlling the transversal alignment and longitudinal alignment of the radiation focus are represented as an integral component. In another embodiment, the components may be disposed separately along the direction of propagation of the laser beam 20. Thus, for example, an adjustable mirror may be disposed in front of the beam expansion optical system 22, in the direction of propagation, for the purpose of controlling the longitudinal alignment of the radiation focus.

The mirror 26 is an immovable deflection mirror, which is designed to direct the laser beam 20 in the direction of the focusing objective 28. In addition or as an alternative to this, further optical mirrors and/or optical elements, for deflecting and diffracting the laser beam 20, may be disposed in the beam path.

The focusing objective 28 is designed to focus the laser beam 20 on to the region of the cornea of the eye 12 to be treated. The focusing objective 28 in this case may be, for example, an F-Theta objective. The focusing objective 28 is detachably coupled to the patient adapter 17. The patient adapter 17 comprises a conical carrier sleeve 30, which is connected to the focusing objective 28 via a coupling formation (not represented), and a contact element 32, which is attached to the narrower underside of the carrier sleeve 30 that faces towards the eye 12. The contact element 32 in this case may be attached to the carrier sleeve 30 in a non-detachable manner (e.g. by adhesive bonding) or in a detachable manner (e.g. by screwed connection). The contact element 32 has an underside, denoted as a bearing contact surface 34, which faces towards the eye 12. In the embodiment shown, the bearing contact surface 34 is realized as a planar surface. During the laser treatment of the eye 12, the contact element 32 is pressed against the eye 12, or the eye 12 is sucked on to the bearing contact surface 34 by negative pressure, in such a manner that at least the region of the cornea of the eye 12 to be treated is flattened.

The control device 14 comprises a memory 36, in which at least one control program 38, having program instructions, is stored. The laser source 18 and the scanner device 24 are controlled by the control device 14 in accordance with the program instructions. The control program 38 in this case contains program instructions that, when executed by the control device 14, cause the radiation focus to be moved in time and space in such a manner that an incision figure is produced in the cornea of the eye 12 to be treated. The incision figure may comprise a LASIK flap and additional auxiliary channels for avoiding an OBL.

Figure 2B:
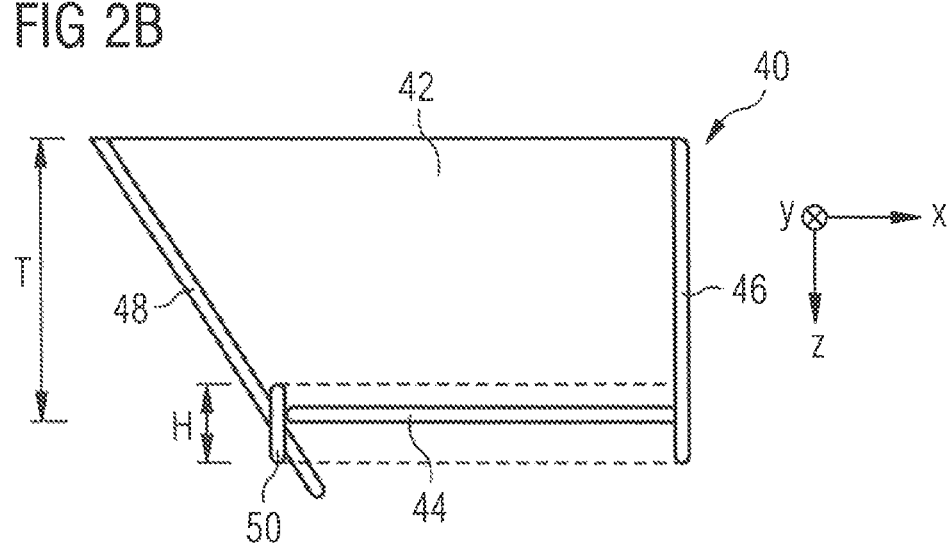

FIGS. 2A and 2B show embodiments of a corneal incision figure, denoted in general by 40, in a laser treatment of the eye 12. The laser treatment may be performed by means of the device shown in FIG. 1. FIG. 2A shows a top view, and FIG. 2B shows a cross-sectional view of the corneal incision FIG. 40.

In FIG. 2A, a flattening region is denoted by a circle line 41 indicated by long line segments. The flattening region 41 describes the region of the eye 12 that bears on the bearing contact surface 34 of the contact element 32 and that is flattened for laser treatment (cf. FIG. 1). The flattening region 41 may have a contour other than a circle. The contour is influenced, for example, by differing radii of curvature in the main meridian directions of the surface of the cornea.

The incision FIG. 40 represented defines a flap, which is denoted in general by 42. The flap 42 comprises a flap underside, which is parted off by a bed incision 44 from adjoining corneal tissue located deeper in the longitudinal direction, starting from the surface of the cornea, and a flap sheath that is parted off by a lateral incision 46 from corneal tissue that adjoins in the transversal direction.

In the embodiment shown, the bed incision 44 extends over a circle segment of a circle area, the circle segment being delimited by an approximately rectilinear chord of a circle and by an arcuate circle arc. In another embodiment, the bed incision 44 may extend over an entire circle area, or the arcuate edge portion may be other than a circle arc (e.g. elliptical). In the embodiment shown, the lateral incision 46 extends along the entire arcuate edge portion of the bed incision 44. In the region of the rectilinearly extending edge portion of the bed incision 44, the flap 42 is connected to the adjoining corneal tissue in less deep regions, relative to the bed incision 44. The transition region (hinge region) between the flap 42 and the adjoining corneal tissue forms a hinge that allows the flap 42 to fold away in such a manner that the deeper corneal tissue is exposed for an ablating laser treatment. In the embodiment shown, a notional hinge axis A of the hinge corresponds approximately to the rectilinearly extending edge portion of the bed incision 44.

For the purpose of removing gases that develop during the production of the bed incision, the incision FIG. 40 additionally comprises a first auxiliary channel 48 and a second auxiliary channel 50. The course of the first auxiliary channel 48 is outside of the flap 42, going out from the hinge region as far as the eye surface. In this case, in the embodiment shown, the first auxiliary channel 48 has a substantially constant width $W_1$. In another embodiment, the first auxiliary channel 48 may have, for example, a greater width in the hinge region and a lesser width in the region of the eye surface (or vice versa).

In order that the gases are removed rapidly and completely from the region of the bed incision 44, the second auxiliary channel 50 is provided, via which the gases get into the first auxiliary channel 48 in a simplified manner. In the embodiment shown, the second auxiliary channel 50 runs continuously along the entire edge of the bed incision 44. It is thereby possible, in particular, to improve the removal of gases from regions of the bed incision 44 that are produced closer to the edge portion of the bed incision 44 that is opposite the hinge region. The second auxiliary channel 50 in this case has a channel portion extending rectilinearly in the hinge region, and a channel portion extending in the form of an arc outside of the hinge region. In another embodiment, it may be provided that the second auxiliary channel 50 does not extend along the entire edge of the bed incision 44. It may be provided, for example, that the rectilinearly extending channel portion of the second auxiliary channel 50 extends only within the portions of the hinge region in which the first auxiliary channel 48 does not extend (as explained more fully in the following with reference to FIG. 3B).

It may be provided that the second auxiliary channel 50 has a width $W_2$ that is substantially constant along its direction of extent. The width $W_2$ may correspond to a single photodisruptive damage zone or to a plurality thereof positioned next to each other. The width $W_2$ may assume, for example, values of approximately 5 μm or 10 μm.

FIG. 2B shows a cross-sectional view of the corneal incision FIG. 40 in the flattening region 41 of the eye according to FIG. 2A, along a straight line within a region delimited by the dotted lines in FIG. 2A.

In the embodiment shown, the bed incision 44 extends out from the surface of the cornea at a substantially constant corneal depth. The depth of the bed incision 44 in this case corresponds to the desired thickness T of the flap 42. In this case, the thickness T may assume, for example, values in the range of from 60 µm to 150 µm, such as, for example, 60 µm, 80 µm, 100 µm, 120 µm or 150 µm. As an alternative to this, the flap 42 may have, for example, a lesser thickness in the hinge region and a greater thickness in the region opposite the hinge region (or vice versa). It may be provided that the height of the bed incision 44 corresponds to a single damage zone produced by photodisruption. In this case, the height may be approximately 5 µm.

The second auxiliary channel 50 has a height H that is substantially constant over its length, as shown in FIG. 2B by the incisions through the second auxiliary channel 50 that are represented on opposite sides of the bed incision 44. In order to simplify the removal of the gases through the second auxiliary channel 50, in the embodiment shown the channel height H corresponds to a plurality of damage zones, produced by photodisruption, that are disposed one above the other. Thus, the channel height H may assume, for example, values of not less than 5 µm or 10 µm or 15 µm. Moreover, the channel height H may correspond to not more than 35 µm or 30 µm or 25 µm. In another embodiment, a channel height H that varies over the length of the second auxiliary channel 50 may be provided.

In the embodiment shown, the second auxiliary channel 50 reaches into deeper corneal regions and less deep corneal regions, relative to the bed incision 44. In this case, it may be provided that the second auxiliary channel 50 is produced in such a depth that the bed incision 44 adjoins the second auxiliary channel 50 approximately in the region of the central longitudinal extent of the latter. In another embodiment, the second auxiliary channel 50 may reach, for example, only into deeper corneal regions or only into less deep corneal regions, relative to the bed incision 44.

The first auxiliary channel 48 extends from the surface of the cornea into corneal depths beneath the bed incision 44 (as also represented in FIG. 2A by the dashed line indicated by short line segments). In this case, it can extend, for example, into regions that are deeper by 5 µm, 10 µm, 15 µm or 20 µm. Gases can be stored temporarily in the portion of the first auxiliary channel 48 located beneath the bed incision 44. It is thus possible, for example, to avoid accumulation of gases in the region of the bed incision when the removal capacity of the portion of the first auxiliary channel 48 located above the bed incision 44, has been exhausted.

The first auxiliary channel 48 is connected to the bed incision 44 and to the second auxiliary channel 50. In the embodiment shown, it is provided that the first auxiliary channel 48 adjoins the edge of the bed incision 44 in the hinge region. In another embodiment, it may be provided that the first auxiliary channel 48 does not adjoin the edge of the bed incision 44, and is connected to the bed incision 44, for example, via the connection to the second auxiliary channel 50.

In the embodiment shown, the lateral incision 46 adjoins the second auxiliary channel 50 rectilinearly, and leads as far as the surface of the cornea. In an alternative embodiment, the lateral incision 46 may also lead obliquely to the eye surface. An angle between the second auxiliary channel 50 and the lateral incision 60 may assume values of between 140° and 180°, such as, for example, 140°, 160° or 180°. The width of the lateral incision 46 may correspond to the width $W_2$ of the second auxiliary channel 50, or differ from it. The width of the lateral incision 46 may correspond, for example, to a single damage zone produced by photodisruption.

FIGS. 3A and 3b show embodiments of scan patterns of the movement of the radiation focus according to the time sequence, provided by the program instructions, for producing the incision FIG. 40 (e.g. according to FIGS. 2A and 2B). The bed incision 44, the first auxiliary channel 48 and the second auxiliary channel 50 are represented.

In the embodiments shown, the program instructions provide for the production of the first auxiliary channel 48 before the production of the flap 42, and then the production of the second auxiliary channel 50. Thus, even before commencement of the production of the bed incision 44, a possibility exists for removing the gases, developed during the production of the bed incision 44, out of the region of the bed incision 44, to the surface of the cornea.

For the purpose of producing the first auxiliary channel 48, the radiation focus progresses, scan line by scan line, out from the surface of the cornea in the direction of regions located deeper in the cornea, as indicated by the arrow 60 shown in FIG. 3A. The scan lines, denoted by 62, run, approximately rectilinearly and parallel to each other, transversely in relation to the direction of extent of the first auxiliary channel 48. In another embodiment, the scan lines 62 may run in the direction of extent of the first auxiliary channel 48. The portion of the first auxiliary channel 48 that extends into corneal depths beneath the bed incision 44 is not represented, for reasons of clarity.

In the embodiment shown in FIG. 3A, the second auxiliary channel 50 forms a closed annular channel (cf. also FIG. 2A). For this purpose, starting from one end of the hinge region, the channel portion that runs rectilinearly in the hinge region is produced first, and then the channel portion that runs in the form of an arc outside of the hinge region is produced, as marked by the arrows denoted by 64.

Unlike FIG. 3A, in the embodiment shown in FIG. 3B the second auxiliary channel 50 does not run within the portion of the hinge region into which the first auxiliary channel 48 extends. Starting from a first edge of the first auxiliary channel 48 (marked by the point 66), the rectilinear channel portion in the hinge region that adjoins in the negative y direction is produced first, then the channel portion running in the form of an arc outside of the hinge region is produced, and finally a second channel portion of the second auxiliary channel 50 is produced, which portion extends as far as a second edge of the first auxiliary channel 48 (marked by the point 68) that is opposite the first edge. The direction in which the second auxiliary channel 50 is produced is indicated by the arrows 70. The first auxiliary channel 48 is connected to the second auxiliary channel 50, at least in the edge region (points 66, 68).

In another embodiment, a movement of the radiation focus that differs from the embodiments shown in FIGS. 3A and 3B may be provided by the program instructions. For example, the closed annular channel according to FIG. 3A may be produced starting from a point within the portion of the hinge region into which the first auxiliary channel 48 extends. Moreover, the direction of the focus movement indicated by the arrows may be reversed, at least partially.

For the purpose of producing the flap 42, the bed incision 44 is first applied. In the embodiments shown in FIGS. 3A and 3B, the bed incision 44 is produced, in accordance with the program instructions, by means of a movement of the radiation focus along rectilinear and mutually parallel scan lines, whose line direction runs approximately perpendicularly in relation to the hinge axis A. In accordance with a provided time sequence of the program instructions, a first scan line 72 is firstly produced with reference to the control of the radiation focus according to FIG. 1, which scan line corresponds to a notional bed-incision central line that is perpendicular to the hinge axis A. The radiation focus then progresses from one scan line to the respectively next scan line, starting from the bed-incision central line, in the positive or negative y direction, and after that in the opposite y direction. The directions of production are indicated by the arrows 74 and 76. It is to be noted that the first scan line 72 may have the same transversal extent as the other scan lines of the bed incision 44, and is represented in a more pronounced manner only for reasons of clarity. In an alternative embodiment, it may be provided that the portions of the bed incision 44 reaching out from the bed-incision central line 72 in the positive and the negative y directions are applied approximately simultaneously. For this purpose, for example, the device 10 according to FIG. 1 could additionally comprise an arrangement for splitting the laser beam 20, and supplementary arrangements for controlling the radiation focus in the transversal and longitudinal directions, and for focusing the laser beam 20.

Furthermore, for example, a time sequence for the movement of the radiation focus may be provided, according to which the radiation focus progresses, scan line by scan line, starting from a point of minimum y extent of the bed incision 44, in the direction of maximum y extent (or vice versa).

In another embodiment, it may be provided that the line direction of the scan lines corresponds, at least approximately, to the direction of the hinge axis A. In this case, the production of the bed incision may follow a time sequence of the movement of the radiation focus, according to which the radiation focus progresses, for example, scan line by scan line, increasingly in the direction away from the hinge region.

It may be provided that the lateral incision 46 (not represented) is produced after the bed incision 44, or that the lateral incision 46 is produced after the second auxiliary channel 50 and before the bed incision 44. It is to be noted that no limitation whatsoever to a particular time sequence of incision production and channel production is intended.

The invention claimed is:

1. An apparatus for laser treatment of a human eye, comprising:
   a source of pulsed laser radiation;
   a control device configured to control a focus of the laser radiation in space and time to generate an incision figure that defines:
      a corneal flap connected to adjoining corneal tissue in a hinge region and having a flap underside parted-off from adjoining corneal tissue by a bed incision;
      a first auxiliary channel extending from the hinge region to an outer surface of the eye and adapted to remove gases that develop during the generation of the bed incision, the first auxiliary channel extending to a corneal depth beneath the bed incision;
      a second auxiliary channel extending along an edge of the bed incision and having a channel portion extending rectilinearly in the hinge region, the second auxiliary channel having a substantially constant width and a channel height of not less than 15 μm, the second auxiliary channel connected to the first auxiliary channel and extending beyond the hinge region, the second auxiliary channel extending into a corneal region beneath the bed incision, the extension of the second auxiliary channel beneath the bed incision distinct from the extension of the first auxiliary channel beneath the bed incision, the second auxiliary channel generated prior to the bed incision; and
      a lateral incision that parts a flap edge of the flap from adjoining corneal tissue, the lateral incision located outside of the hinge region, the lateral incision adjoining and produced after the second auxiliary channel.

2. The apparatus according to claim 1, wherein the second auxiliary channel extends continuously into a region of the bed incision edge that is opposite the hinge region.

3. The apparatus according to claim 1, wherein the second auxiliary channel extends continuously over the entire part of the bed incision edge that is located outside of the hinge region.

4. The apparatus according to claim 1, wherein:
   the second auxiliary channel is configured to form a closed annular channel, and
   the annular channel extends in the form of an arc outside of the hinge region.

5. The apparatus according to claim 1, wherein the second auxiliary channel has a height that is substantially constant over its length.

6. The apparatus according to claim 1, wherein the second auxiliary channel has a channel height of not more than 25 μm.

7. The apparatus according to claim 1, wherein the control device is configured to generate the lateral incision after the bed incision.

8. The apparatus according to claim 7, wherein the lateral incision extends to the eye surface.

9. The apparatus according to claim 7, wherein the lateral incision adjoins the second auxiliary channel rectilinearly.

10. The apparatus according to claim 1, wherein the control device is configured to generate the bed incision through movement of the focus along a plurality of mutually parallel, rectilinear scan lines, wherein line directions of the scan lines extend transversely with respect to an imaginary hinge axis of the hinge region.

11. The apparatus according to claim 10, wherein the scan lines extend at least perpendicularly with respect to the hinge axis.

12. The apparatus according to claim 10, wherein the control device is configured to cause, for a first group of scan lines, a progression of the focus from a scan line to a respectively next scan line of the first group in a first direction and, for a second group of scan lines, a progression of the focus from a scan line to a respectively next scan line of the second group in a direction opposite to the first direction.

13. The apparatus according to claim 12, wherein:
   an area of the bed incision is substantially divided by the first and second groups into halves adjoining one another at an imaginary center line perpendicular to the hinge axis, and
   for each of the first and second groups the progression of the focus is effected in a direction away from the center line.

14. A method for laser treatment of a human eye, comprising steps of:
   providing pulsed laser radiation;
   directing the laser radiation at a human cornea to be treated;

controlling a focus of the laser radiation in space and time to:
  generate a corneal flap connected to adjoining corneal tissue in a hinge region and having a flap underside parted-off from adjoining corneal tissue by a bed incision and a lateral incision;
  generate a first auxiliary channel extending from the hinge region to an outer eye surface and adapted to remove gases that develop during the generation of the bed incision, the first auxiliary channel extending to a corneal depth beneath the bed incision;
  generate a second auxiliary channel extending along an edge of the bed incision, wherein the second auxiliary channel is connected to the first auxiliary channel and extends beyond the hinge region, the second auxiliary channel extending into a corneal region beneath the bed incision, the extension of the second auxiliary channel beneath the bed incision distinct from the extension of the first auxiliary channel beneath the bed incision, the second auxiliary channel generated prior to the bed incision and the lateral incision; and
  move the focus of the laser radiation along a plurality of mutually parallel, rectilinear scan lines to generate the bed incision, the line directions of the scan lines extending transversely with respect to an imaginary hinge axis of the hinge region, the focus moved to create:
    for a first group of scan lines, a progression of the focus from a scan line to a respectively next scan line of the first group in a first direction, and
    for a second group of scan lines, a progression of the focus from a scan line to a respectively next scan line of the second group in a direction opposite to the first direction.

15. The method according to claim 14, wherein the second auxiliary channel extends continuously into a region of the bed incision edge that is opposite the hinge region.

16. The method according to claim 14, wherein the second auxiliary channel extends continuously over the entire part of the bed incision edge that is located outside of the hinge region.

17. The method according to claim 14, wherein the second auxiliary channel forms a closed annular channel, wherein the annular channel has a channel portion extending rectilinearly in the hinge region and extends in the form of an arc outside of the hinge region.

18. The method according to claim 14, wherein:
  the flap has a flap edge that is parted off from adjoining corneal tissue by a lateral incision located outside of the hinge region;
  the lateral incision is generated after the bed incision; and
  the lateral incision adjoins the second auxiliary channel and extends to the eye surface.

19. The method according to claim 14, wherein:
  the flap has a flap edge that is parted off from adjoining corneal tissue by a lateral incision located outside of the hinge region;
  the lateral incision is generated after the bed incision; and
  the lateral incision adjoins the second auxiliary channel rectilinearly.

20. The method according to claim 14, wherein an area of the bed incision is substantially divided by the first and second groups into halves adjoining one another at an imaginary center line perpendicular to the hinge axis, wherein for each of the first and second groups the progression of the focus is effected in a direction away from the center line.

* * * * *